US011642136B2

(12) United States Patent
Sauter et al.

(10) Patent No.: US 11,642,136 B2
(45) Date of Patent: May 9, 2023

(54) SURGICAL CLIP

(71) Applicant: Aesculap AG, Tuttlingen (DE)

(72) Inventors: Wolfgang Sauter, Renquishausen (DE);
Thomas Pleil, Bad Duerrheim (DE)

(73) Assignee: Aesculap AG, Tuttlingen (DE)

( * ) Notice: Subject to any disclaimer, the term of this patent is extended or adjusted under 35 U.S.C. 154(b) by 47 days.

(21) Appl. No.: 16/947,638

(22) Filed: Aug. 11, 2020

(65) Prior Publication Data
US 2020/0367892 A1 Nov. 26, 2020

Related U.S. Application Data

(63) Continuation of application No. PCT/EP2019/054274, filed on Feb. 21, 2019.

(30) Foreign Application Priority Data

Feb. 21, 2018 (DE) ..................... 10 2018 103 903.4

(51) Int. Cl.
*A61B 17/122* (2006.01)
*A61B 17/12* (2006.01)

(52) U.S. Cl.
CPC .... *A61B 17/1227* (2013.01); *A61B 17/12113* (2013.01)

(58) Field of Classification Search
CPC ..... A61B 17/08; A61B 17/083; A61B 17/122; A61B 17/1227; A61B 2017/081
See application file for complete search history.

(56) References Cited

U.S. PATENT DOCUMENTS

| 3,827,438 | A | * | 8/1974 | Kees, Jr. ............ A61B 17/1227 24/545 |
| 4,340,061 | A | | 7/1982 | Kees, Jr. et al. |
| 4,484,581 | A | | 11/1984 | Martin et al. |
| 4,796,625 | A | | 1/1989 | Kees, Jr. |
| 4,932,955 | A | * | 6/1990 | Merz .................. A61B 17/1227 606/158 |

(Continued)

FOREIGN PATENT DOCUMENTS

| CA | 2587267 | 10/2007 |
| DE | 3139488 | 4/1983 |

(Continued)

*Primary Examiner* — Kathleen S Holwerda
(74) *Attorney, Agent, or Firm* — Lipsitz & McAllister, LLC

(57) ABSTRACT

The present invention relates to a surgical clip, comprising a first clamping arm, a second clamping arm, and a biasing element, which first clamping arm defines a first clamping surface, which second clamping arm defines a second clamping surface, and which biasing element holds the first clamping surface and the second clamping surface against each other in a basic position, in particular under bias, wherein the first and the second clamping arm are pivotable against each other counter to the action of the biasing element, wherein the biasing element is configured in the form of a coil spring which defines a coil spring longitudinal axis and has a first coil spring end and a second coil spring end, wherein the coil spring comprises between the first coil spring end and the second coil spring end at least one winding extending over a circumferential angle of more than 360°.

19 Claims, 10 Drawing Sheets

(56) References Cited

U.S. PATENT DOCUMENTS

Figure 1A:
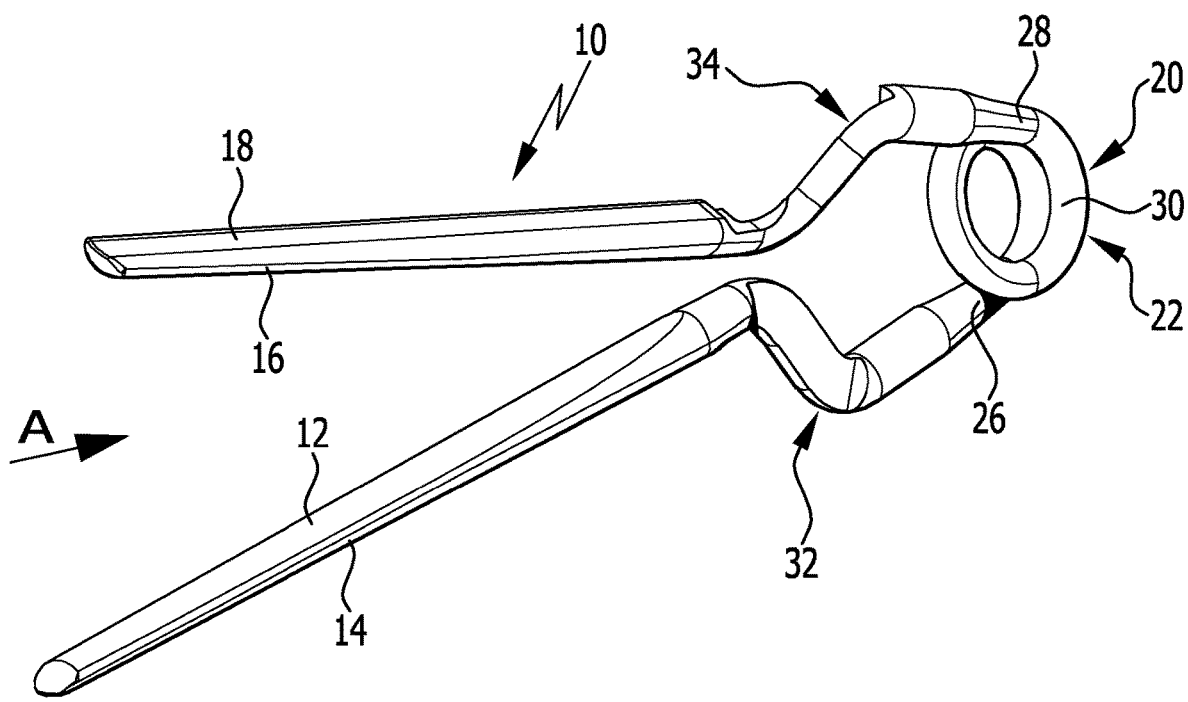

| | | |
|---|---|---|
| 4,961,743 A | 10/1990 | Kees, Jr. et al. |
| 6,179,850 B1 | 1/2001 | Goradia |
| 2003/0199888 A1 | 10/2003 | Lutze et al. |
| 2007/0191883 A1 | 8/2007 | Lazic et al. |
| 2011/0288571 A1 | 11/2011 | Steinhilper et al. |
| 2013/0184726 A1 | 7/2013 | Weisshaupt et al. |
| 2014/0194908 A1 | 7/2014 | Lazic |
| 2015/0057684 A1 | 2/2015 | Zieris |
| 2015/0164510 A1 | 6/2015 | Pleil et al. |
| 2016/0157867 A1 | 6/2016 | Zieris et al. |

FOREIGN PATENT DOCUMENTS

| | | |
|---|---|---|
| DE | 4000086 | 7/1990 |
| DE | 19827093 | 1/2000 |
| DE | 20107378 | 8/2001 |
| DE | 102004016859 | 10/2005 |
| DE | 202006002436 | 6/2006 |
| DE | 202006010414 | 9/2006 |
| DE | 102013107876 | 1/2015 |
| EP | 2752164 | 7/2014 |
| JP | 5314064 | 4/1978 |
| JP | S5870209 | 5/1983 |
| JP | 2003102736 | 4/2003 |
| JP | 2006305230 | 11/2006 |
| RU | 2102017 | 1/1998 |
| WO | 8706118 | 10/1987 |
| WO | 2007006140 | 1/2007 |
| WO | 2012031949 | 3/2012 |
| WO | 2013160452 | 10/2013 |
| WO | 2014001008 | 1/2014 |

\* cited by examiner

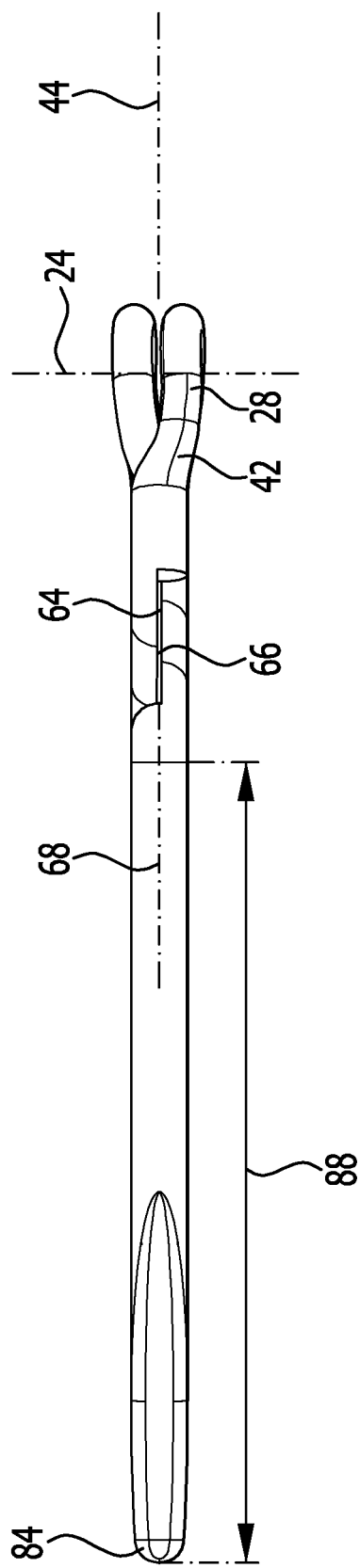
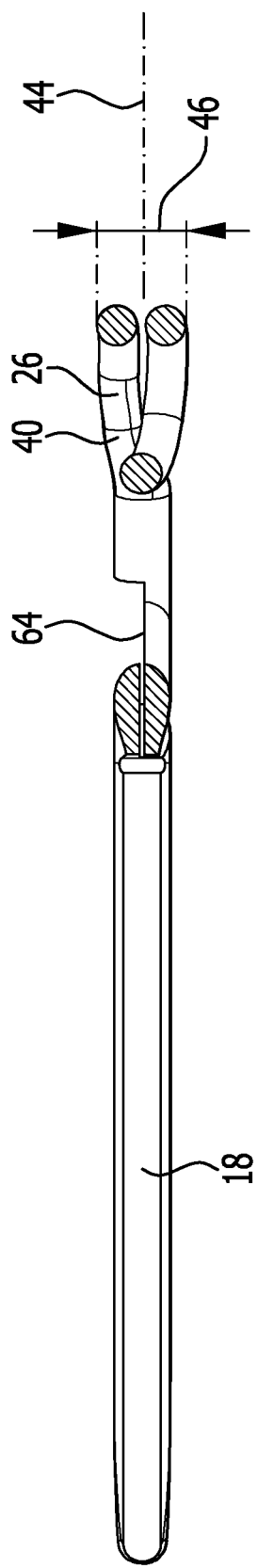

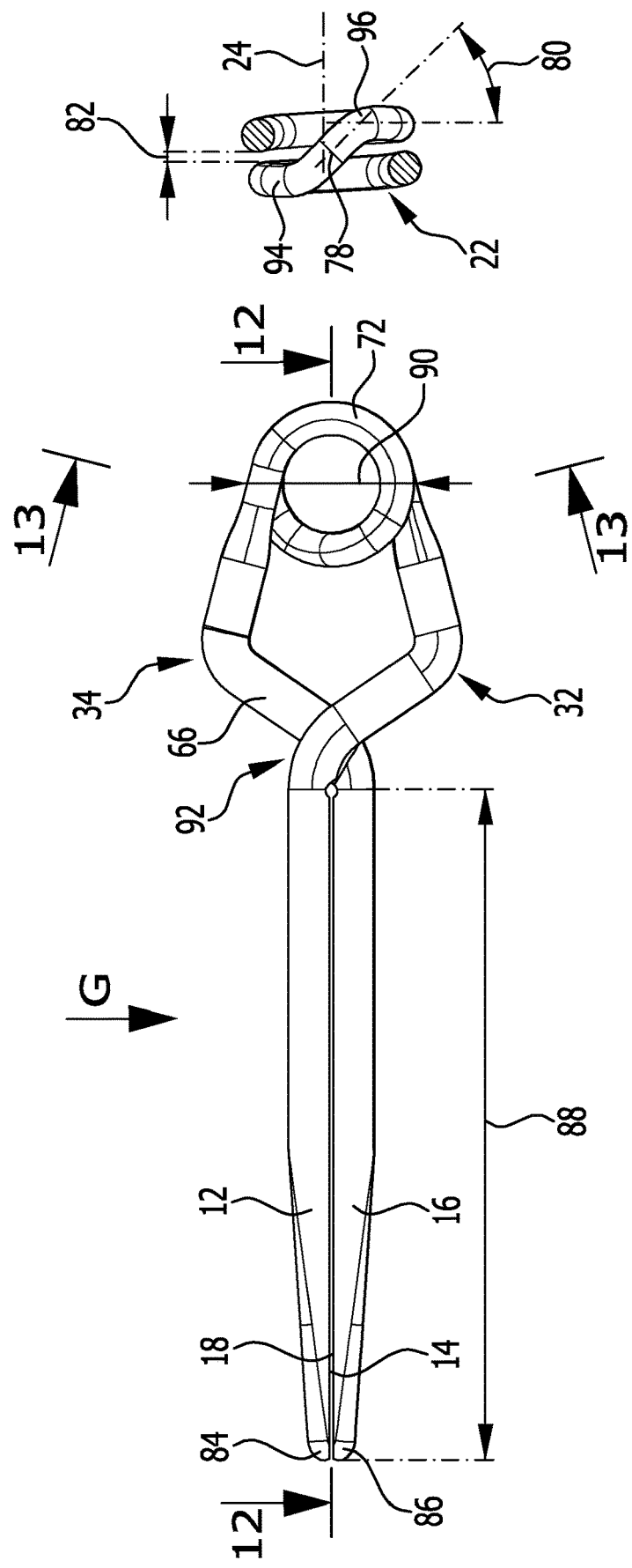

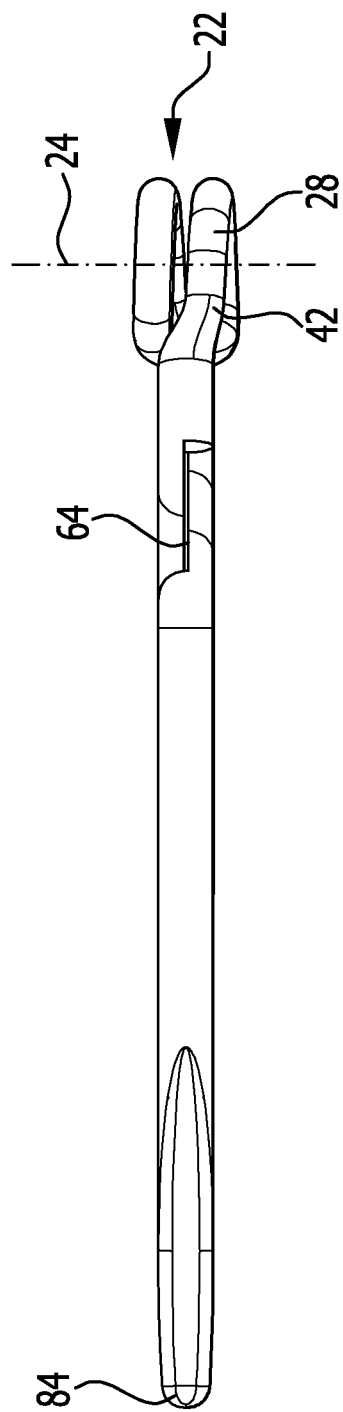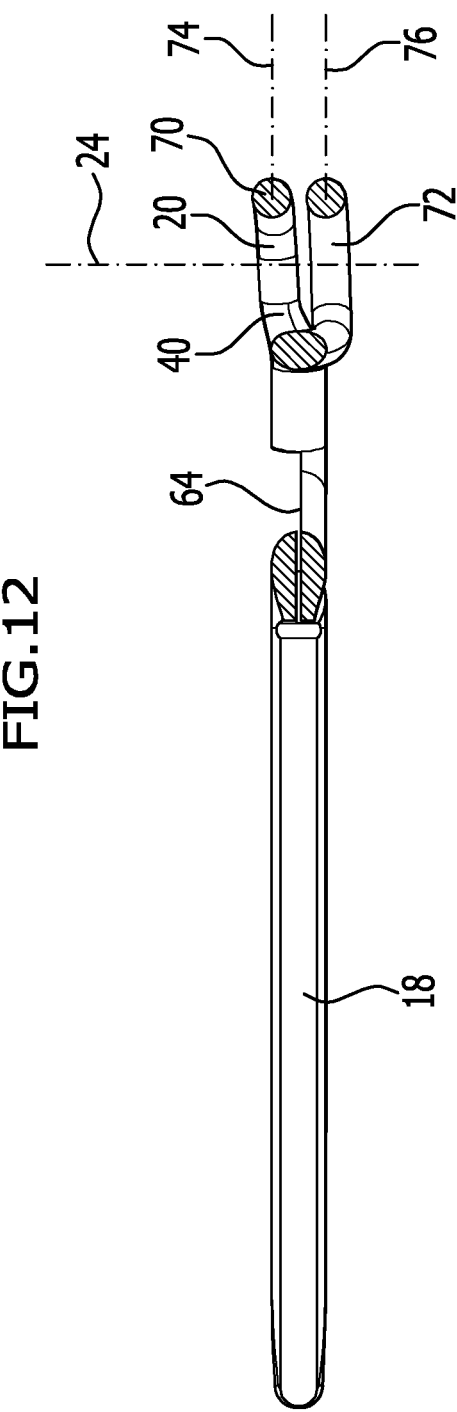

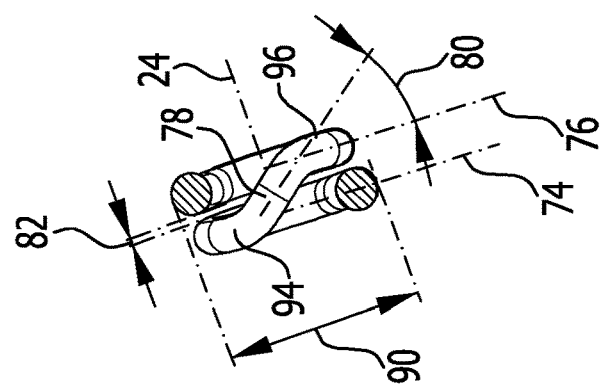
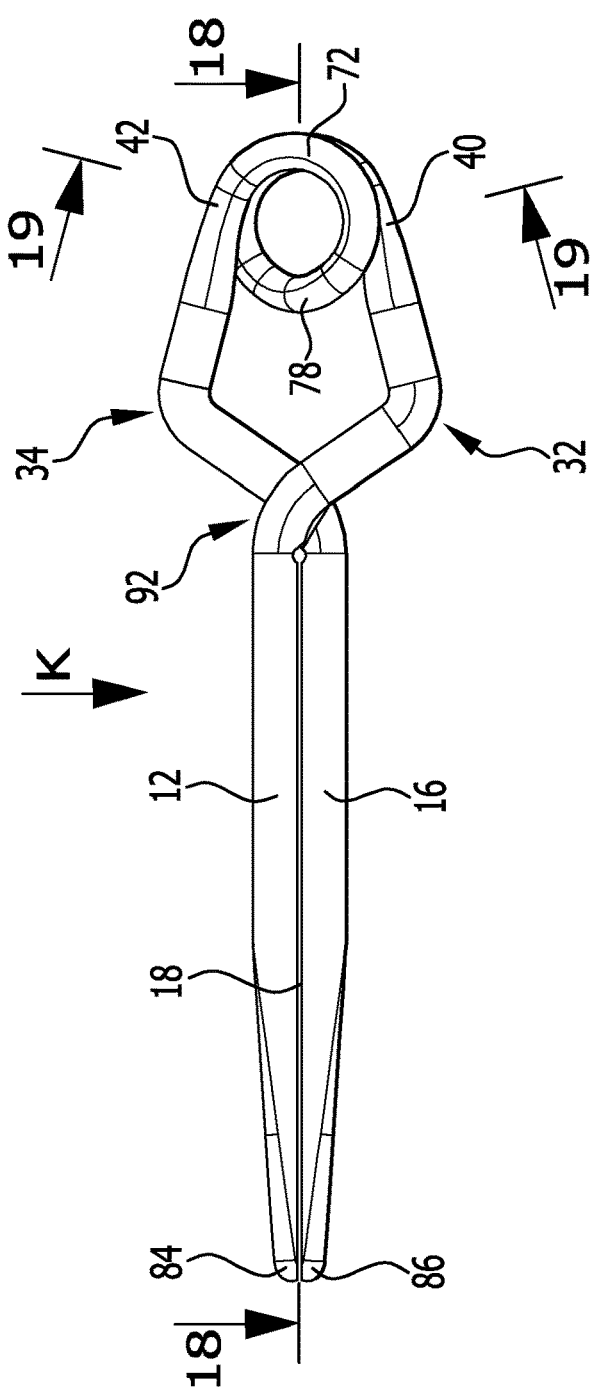

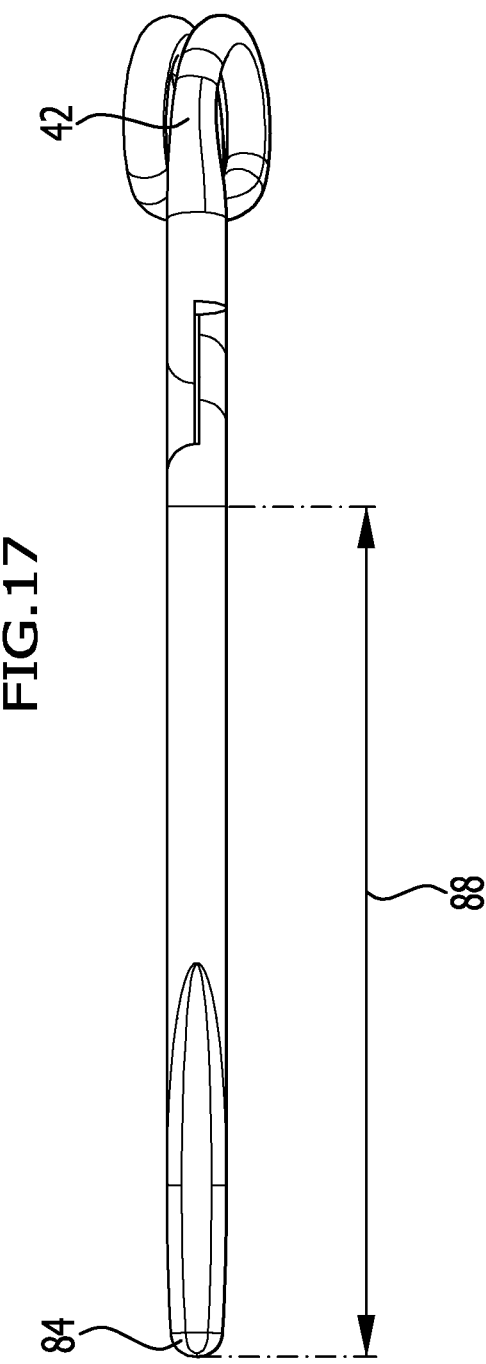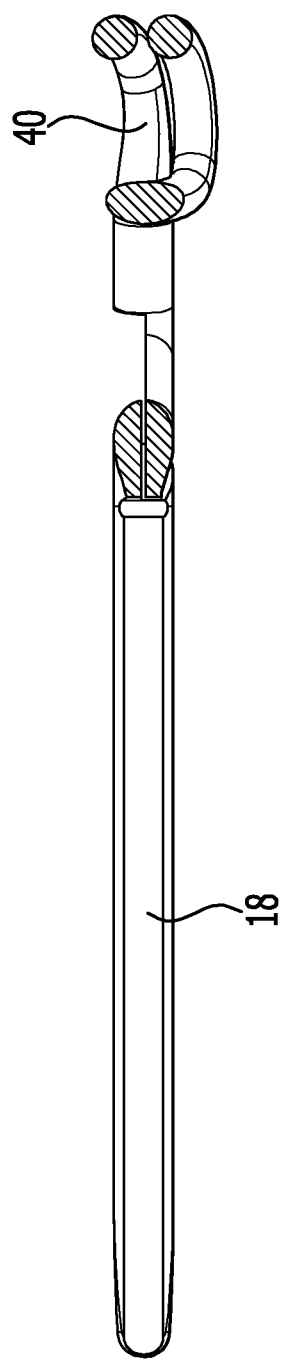

SURGICAL CLIP

CROSS-REFERENCE TO RELATED APPLICATIONS

This application is a continuation of international application number PCT/EP2019/054274 filed on Feb. 21, 2019 and claims the benefit of German application number 10 2018 103 903.4 filed on Feb. 21, 2018, which are incorporated herein by reference in their entirety and for all purposes.

FIELD OF THE INVENTION

The present invention relates to surgical clips generally, and more specifically to a surgical clip, comprising a first clamping arm, a second clamping arm, and a biasing element, which first clamping arm defines a first clamping surface, which second clamping arm defines a second clamping surface, and which biasing element holds the first clamping surface and the second clamping surface against each other in a basic position, in particular under bias, wherein the first and the second clamping arm are pivotable against each other counter to the action of the biasing element, wherein the biasing element is configured in the form of a coil spring, which defines a coil spring longitudinal axis and has a first coil spring end and a second coil spring end, wherein the coil spring comprises between the first coil spring end and the second coil spring end at least one winding extending over a circumferential angle of more than 360°, wherein the first coil spring end is connected to the first clamping arm by way of a first connecting portion, wherein the second coil spring end is connected to the second clamping arm by way of a second connecting portion, and wherein the clamping surfaces held against each other in the basic position define a clamping plane.

BACKGROUND OF THE INVENTION

Surgical clips of the kind described at the outset are used in surgery, in particular for treating aneurysms. Using such so-called "aneurysm clips", for example aneurysms, i.e. sacculations of hollow organs like e.g. blood vessels, are clamped off by clamping off the sacculation between the clamping surfaces of the two clamping arms.

In known surgical clips, the coil spring is formed between the two connecting portions by means of winding. Depending on the angle at which the two connecting portions project from the coil spring, at least one winding is thus formed, which extends over a circumferential angle of more than 360°, for example over a circumferential angle of more than 500°.

The conventional way of winding the coil spring with a winding extending over a circumferential angle of about 540° results in the problem that the clamping surfaces of the two clamping arms, which are oriented in parallel to each other and are formed at both free ends of an elongated blank, are inclined toward each other by about 15° after winding the coil spring. This can lead to problems in particular when opening and closing the clip, and can lead to the clamping surfaces of the clamping arms not abutting perfectly against each other in the basic position. In addition, the so-called "scissoring effect" may occur, i.e. the clamping arms sliding on one another in a scissor-like manner, as a result of which the hollow organ to be clamped may be damaged.

SUMMARY OF THE INVENTION

In an aspect of the invention, a surgical clip comprises a first clamping arm, a second clamping arm, and a biasing element. Said first clamping arm defines a first clamping surface. Said second clamping arm defines a second clamping surface. Said biasing element holds the first clamping surface and the second clamping surface against each other in a basic position, in particular under bias. The first and the second clamping arm are pivotable against each other counter to the action of the biasing element. The biasing element is configured in the form of a coil spring which defines a coil spring longitudinal axis and has a first coil spring end and a second coil spring end. The coil spring comprises between the first coil spring end and the second coil spring end at least one winding extending over a circumferential angle of more than 360°. The first coil spring end is connected to the first clamping arm by way of a first connecting portion. The second coil spring end is connected to the second clamping arm by way of a second connecting portion. The clamping surfaces held against each other in the basic position define a clamping plane. The coil spring longitudinal axis runs parallel to the clamping plane.

BRIEF DESCRIPTION OF THE DRAWING FIGURES

Figure 1B:
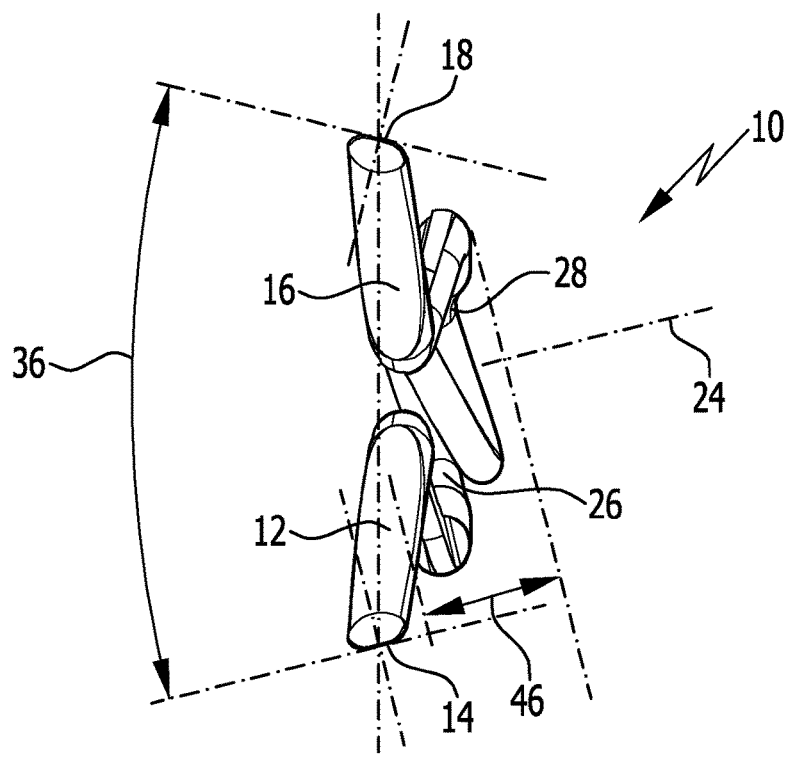
Figure 2:
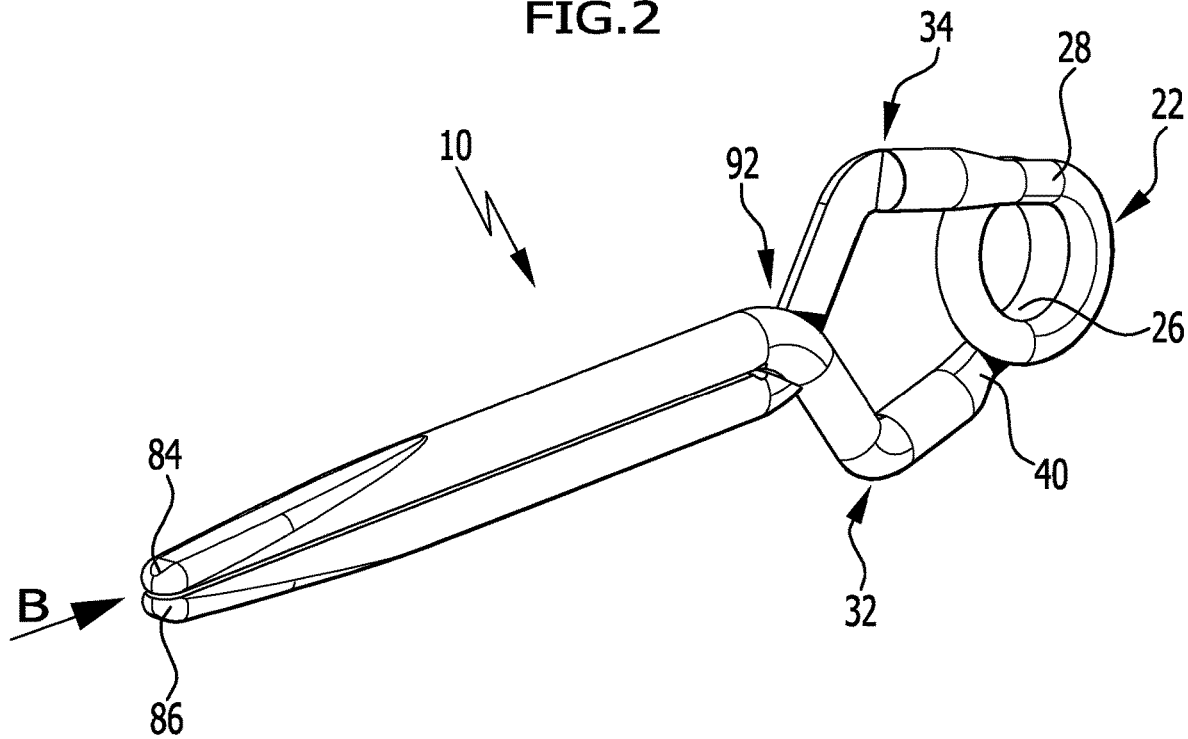
Figure 3:
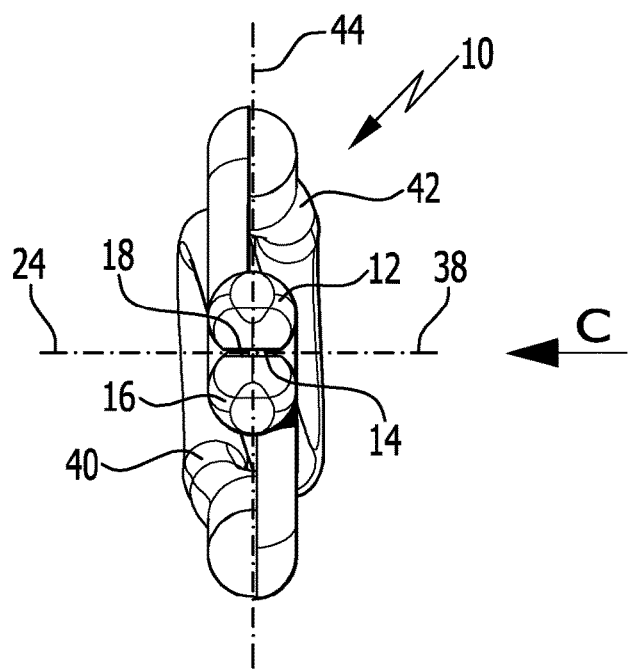
Figure 7:
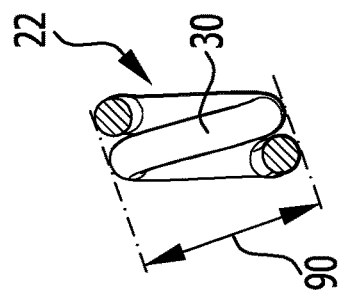
Figure 4:
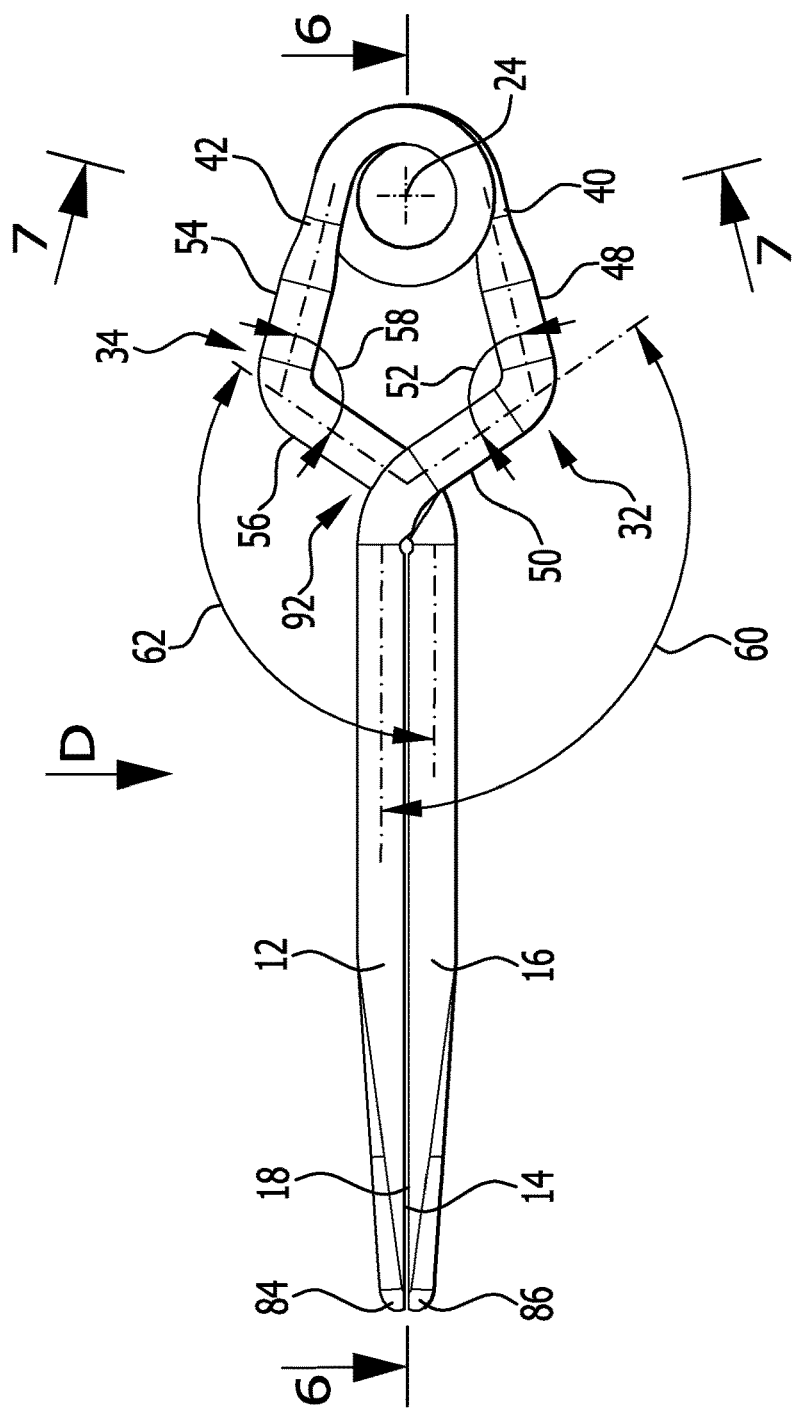
Figure 8:
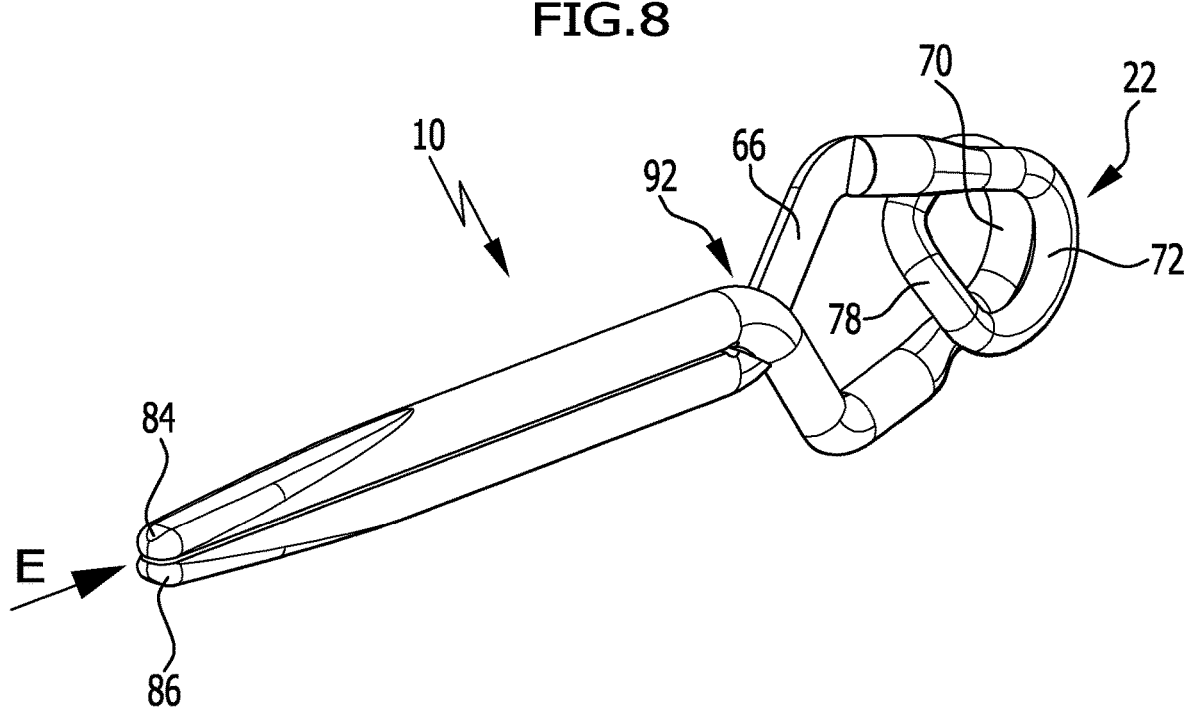
Figure 9:
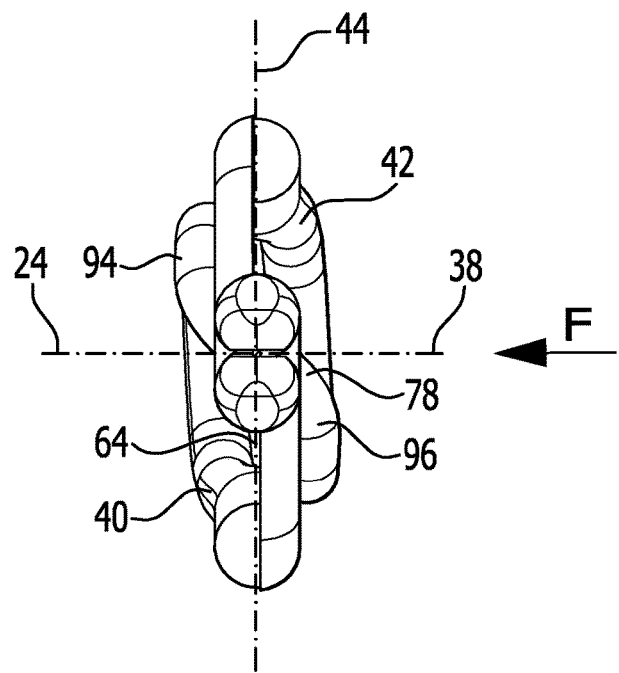
Figure 14:
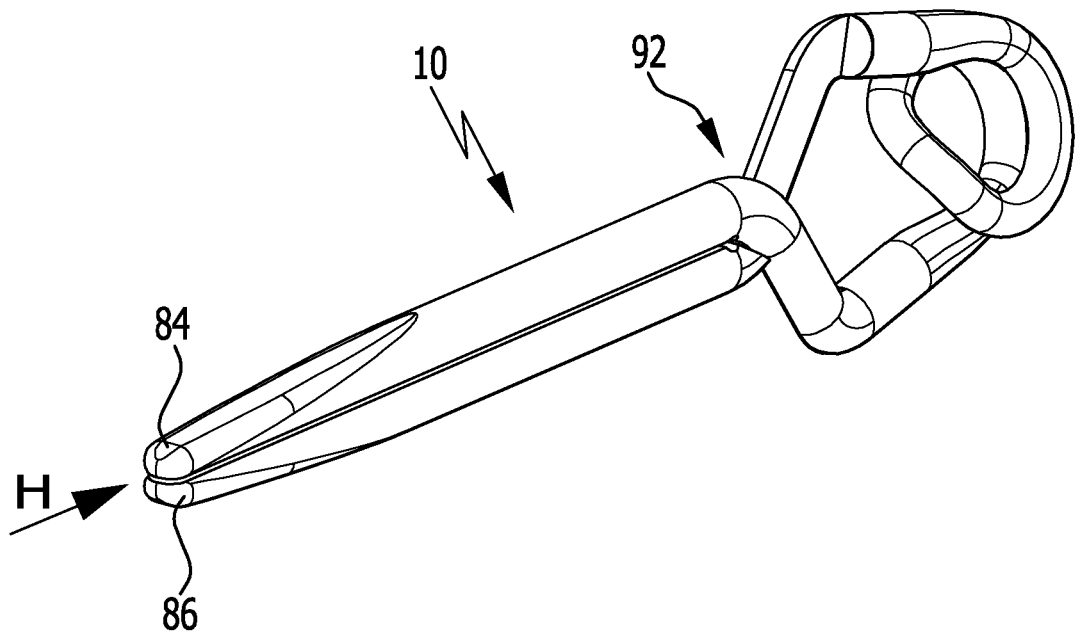
Figure 15:
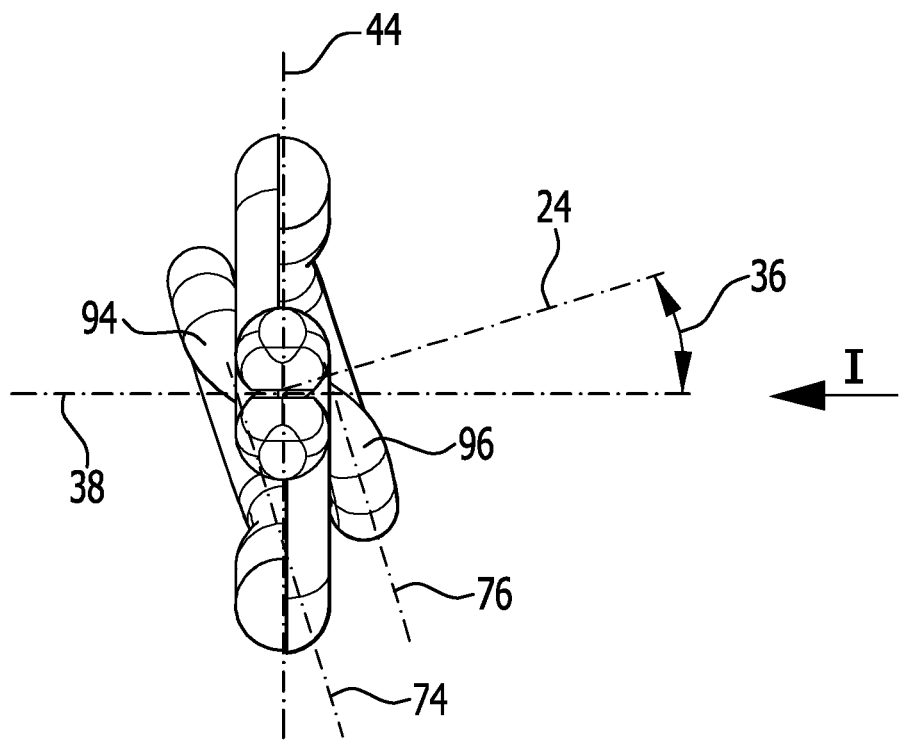

The foregoing summary and the following description may be better understood in conjunction with the drawing figures, of which:

FIG. 1a: shows a perspective view of a surgical clip, as it is known from the prior art, before crossing the two connecting portions or the two clamping arms;

FIG. 1b: shows a view of the arrangement from FIG. 1a in the direction of the arrow A;

FIG. 2: shows a perspective view of a first embodiment of an improved surgical clip;

FIG. 3: shows a view of the clip from FIG. 2 in the direction of the arrow B;

FIG. 4: shows a view of the clip from FIG. 3 in the direction of the arrow C;

FIG. 5: shows a view of the clip from FIG. 4 in the direction of the arrow D,

FIG. 6: shows a sectional view along line 6-6 in FIG. 4;

FIG. 7: shows a sectional view along line 7-7 in FIG. 4;

FIG. 8: shows a perspective view of a second embodiment of an improved surgical clip;

FIG. 9: shows a view of the clip from FIG. 8 in the direction of the arrow E;

FIG. 10: shows a view of the clip from FIG. 9 in the direction of the arrow F;

FIG. 11: shows a view of the clip from FIG. 10 in the direction of the arrow G;

FIG. 12: shows a sectional view along line 12-12 in FIG. 10;

FIG. 13: shows a sectional view along line 13-13 in FIG. 10;

FIG. 14: shows a perspective view of a third embodiment of an improved surgical clip;

FIG. 15: shows a view of the clip from FIG. 14 in the direction of the arrow H;

FIG. 16: shows a view of the clip from FIG. 15 in the direction of the arrow I;

FIG. 17: shows a view of the clip from FIG. 16 in the direction of the arrow K;

FIG. 18: shows a sectional view along line 18-18 in FIG. 16; and

FIG. 19: shows a sectional view along line 19-19 in FIG. 16.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a surgical clip, comprising a first clamping arm, a second clamping arm, and a biasing element, which first clamping arm defines a first clamping surface, which second clamping arm defines a second clamping surface, and which biasing element holds the first clamping surface and the second clamping surface against each other in a basic position, in particular under bias, wherein the first and the second clamping arm are pivotable against each other counter to the action of the biasing element, wherein the biasing element is configured in the form of a coil spring which defines a coil spring longitudinal axis and has a first coil spring end and a second coil spring end, wherein the coil spring comprises between the first coil spring end and the second coil spring end at least one winding extending over a circumferential angle of more than 360°, wherein the first coil spring end is connected to the first clamping arm by way of a first connecting portion, wherein the second coil spring end is connected to the second clamping arm by way of a second connecting portion, and wherein the clamping surfaces held against each other in the basic position define a clamping plane, wherein the coil spring longitudinal axis runs parallel to the clamping plane.

Thus, unlike surgical clips formed in one piece that are available on the market, the coil spring longitudinal axis is not inclined relative to the clamping plane by about 15°, as described above, but rather now runs exactly parallel to the clamping plane. It can thereby be avoided that, unlike in the case of the clamping surfaces of conventional clips, which are inclined to each other, the coil spring does not experience a force component inclined by 15° to the theoretical ideal working direction, which can lead to the coil spring being pressed with its at least one winding "on block". In other words, as a result of the particular orientation of the coil spring longitudinal axis in parallel to the clamping plane, precisely this force component acting on the at least one winding is reduced. Furthermore, an extent of the coil spring in parallel to the coil spring longitudinal axis, i.e. in parallel to the clamping plane, can thus be minimized. A more efficient introduction of force into the coil spring is achieved by means of the described orientation of the coil spring longitudinal axis. In addition, in particular smaller torsional stresses in the coil spring provide greater security and a greater working range thereof. Due to a lesser extent of the coil spring in parallel to the coil spring longitudinal axis, a surgeon has a better view when applying the surgical clip. In addition, in particular, the described "scissoring effect" can be reduced, because the coil spring always acts such that the clamping surfaces of the two clamping arms are pressed against each other perpendicularly.

It is favorable if the first clamping arm has a first free end which points in a direction away from the biasing element or substantially away from the biasing element. This configuration makes it possible in particular to guide the surgical clip laterally over a hollow organ that is to be clamped off.

It is advantageous if the second clamping arm has a second free end which points in a direction away from the biasing element or substantially away from the biasing element. This makes it possible in particular to form a surgical clip which can be guided laterally over a hollow organ in order to clamp off the same.

For an easy handling of the surgical clip, it is favorable if the clip comprises an intersection region and if the first connecting portion and the second connecting portion intersect in the intersection region. In particular, such a configuration makes it possible to open the clip by moving the two connecting portions towards each other. In this way, the clip can be handled by a surgeon in a simple and secure manner.

In accordance with a further preferred embodiment of the invention, provision may be made for the first connecting portion and/or the second connecting portion to have a flattened portion pointing toward the other connecting portion. In particular, two flattened portions may be provided, which abut against each other or are spaced apart from each other by a narrow gap. A particularly compact surgical clip can be formed in this way.

It is advantageous if the flattened portion of the first and/or second connecting portion defines a flattened portion plane, and if the flattened portion plane runs parallel or substantially parallel to the clamping plane. In this way, the surgical clip can in particular be opened and closed in a secure manner, without the two connecting portions necessarily having to contact each other. The flattened portions may in particular serve as a mutual guide for the connecting portions when opening and closing the surgical clip.

It is favorable if the flattened portion of the first connecting portion directly adjoins the first clamping arm and/or if the flattened portion of the second connecting portion directly adjoins the second clamping arm. In this way, the clamping arms are able to abut against each other with the two clamping surfaces in the basic position substantially along the entire longitudinal extent of said clamping arms.

It is favorable if the first connecting portion is angled by a first bend angle between the first clamping arm and the first coil spring end, and/or if the second connecting portion is angled by a second bend angle between the second clamping arm and the second coil spring end. This design makes it possible in particular to configure the first coil spring end and the second coil spring end offset from each other by a circumferential angle of about 180°, and to connect them to the first and the second connecting portion, respectively.

In order to be able to form a symmetrical surgical clip which, in particular, can be handled well, it is advantageous if the first bend angle corresponds to or substantially corresponds to the second bend angle. A surgeon can thus handle the surgical clip intuitively, even if the surgeon is holding said surgical clip rotated by 180° about a longitudinal axis defined by the clamping arms.

The first and/or the second bend angle favorably define an internal angle in a range of about 90° to about 120°. A particularly compact surgical clip can be formed in this way.

In accordance with a further preferred embodiment of the invention, provision may be made for the first connecting portion to be angled by a third bend angle in the transition region to the first clamping arm, and/or for the second connecting portion to be angled by a fourth bend angle in the transition region to the second clamping arm. In this way, it is possible in particular to configure the connecting portion such that it has partial portions spaced at a distance from each other when the clamping surfaces abut against each other in the basic position. These partial portions may then be moved against each other in order to open the clip. At the same time, said partial portions may in particular also mutually form stops which delimit the opening of the surgical clip.

The third bend angle favorable corresponds to or substantially corresponds to the fourth bend angle. Thus, in particular a symmetrical clip can be formed.

Furthermore, provision may in particular also be made for the third bend angle and/or the fourth bend angle to correspond to the first and/or second bend angle. In particular, the first and second bend angles on the one hand and the third and fourth bend angles on the other hand may define alternate angles in the mathematical sense.

It is favorable if the first connecting portion is cranked in the transition region to the first coil spring end and/or if the second connecting portion is cranked in the transition region to the second coil spring end. One or two such cranks in the two described transition regions, in particular to a level which corresponds to half of an extent of the coil spring in parallel to the coil spring longitudinal axis, enables in a simple manner an orientation of the coil spring longitudinal axis in parallel to the clamping plane. As already described above, a force pressing the at least one winding of the coil spring against one another and also an extent of the coil spring in a direction parallel to the coil spring longitudinal axis can thus be minimized. Cranking is to be understood in particular as a single or double angling of the respective connecting portions in relation to the respective coil spring end in order to orient the coil spring longitudinal axis in parallel to the clamping surface.

In accordance with a further preferred embodiment of the invention, provision may be made, in particular also in the case of a surgical clip of the kind described at the outset, for the at least one winding to comprise at least one first winding portion and at least one second winding portion, and for the at least one first winding portion to define a first winding portion plane, and/or for the at least one second winding portion to define a second winding portion plane, and for the at least one first winding portion and the at least one second winding portion to be connected to each other by way of a cranked portion remote from the first coil spring end and from the second coil spring end. The described design makes it possible, in particular, to space the two winding portions at a distance from each other by forming the cranked portion, such that said winding portions do not contact each other. This is achieved in particular by the cranked portion that connects the at least one first winding portion and the at least one second winding portion to each other being arranged between said winding portions, and in this way forming a direct connection of the at least one first winding portion and the at least one second winding portion. In other words, the cranked portion is integrated into the at least one winding. In particular when closing the coil spring, where a diameter thereof is reduced and the at least one winding is moved toward each other in a direction parallel to the coil axis, a blocking of the coil spring by pressing "on block" can be prevented, because adjacent winding portions of the at least one winding are no longer able to come into contact with each other, in particular when opening the surgical clip. In this way, in particular a friction in the region of the coil spring can be minimized, which in particular simplifies opening the surgical clip when said clip has intersecting connecting portions. In addition, the design of the first and second winding portions such that they each define a winding portion plane makes it possible for the coil spring to not be able to twist any further upon a force acting to open the surgical clip, but rather the coil spring is able to contract substantially only in the respective region of the planar winding portions. In particular, a desired distance between the at least one first winding portion and the at least one second winding portion can be set by means of a length and a shape of the cranked portion. In particular, the cranked portion may form a spacer element in order to keep the at least one first winding portion and the at least one second winding portion at a distance from each other so that they do not contact each other, in particular namely independently of whether the clip is closed or open. The surgical clip may of course also have a coil spring with more than two winding portions. In each case two adjacent winding portions are then preferably connected to each other by way of a cranked portion connecting said winding portions.

The surgical clip can be configured particularly simply if the cranked portion is of rectilinear or substantially rectilinear configuration and is connected to the at least one first winding portion angled at a first cranked portion end and is connected to the at least one second winding portion angled at a second cranked portion end. The angling between the cranked portion end and the respective winding portion is preferably identical.

The cranked portion preferably extends transversely to the first and/or second winding portion plane. In particular, it may extend at a cranked portion angle of about 45°. This makes it possible in particular to form the coil spring in the desired manner, namely with winding portions spaced at a distance from each other, without too much plastic deformation.

In order to orient the coil spring longitudinal axis in parallel to the clamping plane in a simple, defined manner, it is favorable if the first coil portion plane and/or the second coil portion plane run perpendicularly to the coil spring longitudinal axis.

It is advantageous if the at least one first winding portion extends over a first winding portion circumferential angle of less than 360°, in particular less than 300°, and/or if the at least one second winding portion extends over a second winding portion circumferential angle of less than 360°, in particular less than 300°. In this way, a coil spring can be formed, in particular with at least two winding portions of that kind, which are oriented in parallel to each other and define coil portion planes that extend perpendicularly to the coil spring longitudinal axis. In particular, the coil spring may also comprise three, four or more winding portions of that kind.

It is advantageous if the at least one first winding portion and the at least one second winding portion are separated from each other by a winding portion gap. As already described above, this design has the advantage that when opening the clip, which has intersecting connecting portions, the coil spring decreases in diameter, adjacent winding portions are not able to come into contact with each other. As a result, a friction in the region between the winding portions of the coil spring can be minimized or even completely avoided. A biasing force exertable by the coil spring can thus be predetermined in a defined manner during production and cannot be inadvertently changed when being applied by a surgeon. The winding portion gap may in particular have a width in a range between 0 mm and about 1 mm.

It is favorable if the coil spring defines a coil spring diameter, if the first clamping arm and the second clamping arm have a clamping arm length, and if the coil spring diameter is less than the clamping arm length. The coil spring diameter is to be understood in particular as a diameter which is defined by the at least one winding of the coil spring, i.e. a diameter in a plane which extends perpendicularly to the clamping plane and perpendicularly to the coil spring longitudinal axis.

In order to be able to clamp a hollow organ securely between the two clamping arms, it is advantageous if the first clamping surface and/or the second clamping surface have a clamping surface structure. In particular, the clamping surface structure may be of macroscopic and/or microscopic configuration. In this way, in particular, the surgical clip can be prevented from sliding off the hollow organ to be clamped.

The surgical clip can be configured in a simple manner if the clamping surface structure comprises clamping projections and/or clamping recesses. In particular, the clamping projections and/or the clamping recesses may be arranged or configured in a linear and/or punctiform manner.

The surgical clip can be configured in a simple and inexpensive manner if it is formed in one piece, in particular monolithically. For example, it may be formed monolithically from one single blank.

It is favorable if the clip is made from a spring steel wire by means of forming. In particular, the spring steel wire may have a circular or substantially circular cross section. The forming may be carried out in particular by means of press forming. The surgical clip can thus be made, in particular, from a blank of a spring steel wire. In particular, the surgical clip may be produced entirely manually or entirely by a machine.

In accordance with a further preferred embodiment of the invention, provision may be made for a cross sectional area of the clip in the region of the coil spring to be smaller than in the region of the first and/or second connecting portion and/or in the region of the first and/or the second clamping arm. Thus, in particular, a particularly compact coil spring can be formed, which also enables e.g. an improved view in an application of the surgical clip to a hollow organ.

FIGS. 1 and 2 show for example a surgical clip, designated as a whole with the reference numeral 10, at it is known from the prior art. It comprises a first clamping arm 12 with a first clamping surface 14 and a second clamping arm 16 with a second clamping surface 18. Furthermore, the clip 10 comprises a biasing element 20 which is configured in the form of a coil spring 22.

The biasing element 20 serves to hold the first clamping surface 14 and the second clamping surface 18 against each other in a basic position, in particular under bias.

However, in FIGS. 1a and 1b, the clip 10 is not depicted in the basic position, but rather with clamping surfaces 14 and 18 not abutting against each other, directly after the production of the clip 10. Due to the action of the coil spring 22, the clamping arms 12 and 16 are spread somewhat apart from each other. After the clamping arms 12 and 16 are crosses, the coil spring 22 then presses the clamping surfaces 14 and 18 against each other under bias.

The coil spring 22 defines a coil spring longitudinal axis 24.

The coil spring 22 has a first coil spring end 26 and a second coil spring end 28.

Between the first coil spring end 26 and the second coil spring end 28, the coil spring 22 comprises at least one winding 30 which extends over a circumferential angle of more than 360°, in the embodiment depicted in FIGS. 1a and 1b over a circumferential angle of about 520°.

The first coil spring end 26 is connected to the first clamping arm 12 by way of a first connecting portion 32. The second coil spring end 28 is connected to the second clamping arm 16 by way of a second connecting portion 34.

When the connecting portions 32 and 34 are moved toward each other, such that the second clamping arm 16 is able to engage under the first clamping arm 12, the clip 10 adopts the basic position. The clamping surfaces 14 and 18 are then substantially in abutment against each other and are held pressed against each other under bias by means of the coil spring 22.

FIG. 1b shows a significant problem with surgical clips as they are known from the prior art. When the clip 10 is formed from a blank of spring steel wire, namely in such a way that with the blank the clamping arms 12 and 16 with clamping surfaces 14 and 18 extending in parallel to each other are formed on free ends of the wire blank, the winding of the coil spring 22 leads to the clamping surfaces 14 and 18 being inclined in relation to each other by an angle 36. This results in the clamping surfaces 14 and 18 in the basic position not abutting against each other in surface-to-surface contact, but rather substantially only with line contact. Thus a corresponding force component acts at the angle 36 of about 15°, which presses mutually abutting regions of the coil spring 22 against each other.

Depicted in FIGS. 2 to 7 is a first embodiment of an improved surgical clip, which is also designated with the reference numeral 10. Identical parts of the clip depicted in FIGS. 2 to 7, which are also already present in the clip 10 known from the prior art and depicted in FIGS. 1a and 1b, are designated with the same reference numerals for the sake of clarity.

The clip 10, as is depicted in FIGS. 2 to 7, differs from the clip of FIGS. 1a and 1b in particular in that the clamping surfaces 14 and 18 in the basic position depicted in FIG. 2 abut in surface-to-surface contact against each other and define a clamping plane 38.

The coil spring longitudinal axis 24 extends, unlike in the case of the clip 10 known from the prior art, in parallel to the clamping plane 38.

To achieve this, the first coil spring end 26 is cranked in the transition region to the first connecting portion 32. In other words, a first crank 40 is formed in order to align the first connecting portion to the coil spring 22. In an analogous manner, a transition region between the second coil spring end 28 and the second connecting portion 34 is cranked, such that a second crank 42 is formed.

It can be easily seen in FIGS. 5 and 6 that the two clamping arms 12 and 16 are arranged symmetrically in relation to a coil spring plane 44 defined by the coil spring 22 due to the two cranks 40 and 42. A maximum thickness 46 of the coil spring 22 in parallel to the coil spring longitudinal axis 24 is therefore less than in the case of the coil spring 10 known from the prior art, which is depicted in FIGS. 1a and 1b.

The first connecting portion 32 comprises two rectilinear portions 48 and 50, which are angled relative to each other by a first bend angle 52. Likewise, the second connecting portion 34 comprises two rectilinear portions 54 and 56, which are angled relative to each other by a second bend angle 58.

The portion 48 directly adjoins the first crank 40, the portion 54 adjoining the second crank 42. The portion 50 is angled relative to the first clamping arm 12 by a third bend angle 60. Analogously, the portion 56 is angled relative to the second clamping arm 16 by a fourth bend angle 62.

The first connecting portion 32 is provided with a flattened portion 64 from the first clamping arm 12 up to the portion 48. In an analogous manner, the second connecting portion 34 is provided with a further flattened portion 66 starting from the second clamping arm 16 up to the portion 54.

The flattened portions 64 and 66 face toward each other and define a common flattened portion plane 68 which extends perpendicularly both to the coil spring longitudinal axis 24 and to the clamping plane 38. The flattened portion plane 68 and the coil spring plane 44 coincide.

The connecting portions 32 and 34 intersect in the region of the flattened portions 64 and 66, whereby an intersection region 92 is defined.

The cranks 40 and 42 serve to orient the clamping surfaces 14 and 18 in parallel to each other, which do not extend in parallel to each other in the case of the clip 10 in accordance with the prior art, as it is depicted for example in FIGS. 1a and 1b, in order to achieve further aforementioned advantages through this configuration.

In the case of the clip 10 depicted in FIGS. 2 to 7, the coil spring 22 is configured identically to the clip 10 depicted in FIGS. 1a and 1b.

Schematically depicted for example in FIGS. 8 to 13 is a second embodiment of an improved surgical clip designated as a whole with the reference numeral 10. It differs from the clip 10 depicted in FIGS. 2 to 7 in the design of the coil spring 22.

In the embodiment of the clip 10 depicted in FIGS. 8 to 13, the coil spring 22 comprises a first winding portion 70 and a second winding portion 72. The first winding portion 70 defines a first winding portion plane 74, the second winding portion 72 defining a second winding portion plane 76.

The first winding portion 70 adjoins the first crank 40, the second winding portion 72 adjoins the second crank 42.

Furthermore, the first winding portion 70 and the second winding portion 72 are directly connected to each other by way of a cranked portion 78. The cranked portion 78 is thus arranged or formed directly between the first winding portion 70 and the second winding portion 72. The cranked portion 78 is of substantially rectilinear configuration and extends transversely to the two winding portion planes 74 and 76, and, in the case of the embodiment of the clip 10 depicted in FIGS. 8 to 13, namely at a cranked portion angle 80 of about 45°.

The cranked portion 78 is angled at a first cranked portion end 94 and is connected to the first winding portion 70. Furthermore, the cranked portion is angled at a second cranked portion end and is connected to the second winding portion 72.

The winding portion planes 74 and 76 extend in parallel to each other and perpendicularly to the coil spring longitudinal axis 24.

As can be seen well in particular in FIG. 8, the winding portions 70 and 72 each extend over a circumferential angle of less than 360°, in particular less than 300°. Rather, said angle is only about 200°.

Due to the cranked portion 78, which has a corresponding length, the two winding portions 70 and 72 are spaced apart from each other and are separated from each other by a winding portion gap 82.

When the connecting portions 32 and 34 are moved toward each other, the coil spring 22 is drawn together. However, it is ensured by the cranked portion 78 that the two winding portions 70 and 72 cannot come into contact with each other, namely independently of an open position of the clip 10 in which the clamping arms 12 and 16 are pivoted away from each other. A friction in the region of the coil spring 22 can thereby be minimized or even completely eliminated.

A third embodiment of an improved surgical clip 10 is schematically depicted in FIGS. 14 to 19. It corresponds in its structure substantially to the second embodiment of the improved clip 10, as it is depicted in FIGS. 8 to 13.

The substantial difference between the clip 10 in accordance with FIGS. 14 to 19 in comparison to the clip in accordance with FIGS. 8 to 13 is that the winding portions 70 and 72 are inclined with their coil portion planes 74 and 76 by the angle 36 in relation to the coil spring plane 44. The coil spring longitudinal axis 24 therefore does not extend in parallel to the clamping plane 38, but rather is inclined in relation thereto by the angle 36.

The clip 10, as it is depicted in FIGS. 8 to 13, thus combines the special characteristics of the coil spring 22 of the clip 10 as it is depicted in FIGS. 2 to 7 with the special characteristics of the coil spring 22 of the clip 10, as it is depicted in FIGS. 14 to 19.

Common to all embodiments of clips 10 depicted in the Figures is that the first clamping arm 12 has a first free end 84 and the second clamping arm 16 has a second free end 86.

The first clamping surface 14 and/or the second clamping surface 18 may optionally have a clamping surface structure, which is not depicted in the Figures. Said clamping surface structure may in particular be of macroscopic or microscopic configuration.

The clamping surface structure may in particular comprise clamping projections and/or clamping recesses. They may in particular be of linear and/or punctiform configuration.

All embodiments of surgical clips 10 depicted in FIGS. 2 to 19 enable an improved handling in comparison with surgical clips 10 known from the prior art. This is due, for one, to the coil spring longitudinal axis 24, which is optionally oriented in parallel to the clamping plane 38, or due to the optionally provided cranked portion 78, which connects the winding portions 70 and 72 directly to each other and keeps the same at a distance from each other in such a way that the winding portion gap 82 is formed.

All improved clips 10 are formed in one piece, namely monolithically.

All improved clips 10 are made from a blank of a spring steel wire, which has a circular or substantially circular cross section.

The improved clips 10 are made by forming the blank, in particular by means of press forming. A cross sectional area of the improved clip 10 in the region of the coil spring 22 is smaller than in the region of the clamping arms 12 and 16.

Further, a clamping arm length 88 of the clamping arms 12 and 16 is greater than a coil spring diameter 90 of the coil spring 22.

REFERENCE NUMERAL LIST 10 clip
12 first clamping arm
14 first clamping surface
16 second clamping arm
18 second clamping surface
20 biasing element
22 coil spring
24 coil spring longitudinal axis
26 first coil spring end
28 second coil spring end
30 winding
32 first connecting portion
34 second connecting portion
36 angle
38 clamping plane
40 first crank
42 second crank
44 coil spring plane 46 thickness
48 portion
50 portion
52 first bend angle
54 portion
56 portion
58 second bend angle
60 third bend angle
62 fourth bend angle
64 flattened portion
66 flattened portion
68 flattened portion plane
70 first winding portion
72 second winding portion
74 first winding portion plane
76 second winding portion plane
78 cranked portion
80 cranked portion angle
82 winding portion gap
84 first free end
86 second free end
88 clamping arm length
90 coil spring diameter
92 intersection region
94 first cranked portion end
96 second cranked portion end

What is claimed is:

1. Surgical clip, comprising:
a first clamping arm,
a second clamping arm, and
a biasing element,
wherein:
the first clamping arm defines a first clamping surface,
the second clamping arm defines a second clamping surface,
the biasing element holds the first clamping surface and the second clamping surface against each other in a basic position,
the first and the second clamping arm are pivotable against each other counter to an action of the biasing element,
the biasing element is configured in the form of a coil spring which defines a coil spring longitudinal axis and has a first coil spring end and a second coil spring end,
the coil spring comprises between the first coil spring end and the second coil spring end at least one winding extending over a circumferential angle of more than 360°,
the first coil spring end is connected to the first clamping arm by way of a first connecting portion,
the second coil spring end is connected to the second clamping arm by way of a second connecting portion,
the clamping surfaces held against each other in the basic position define a clamping plane,
the coil spring longitudinal axis runs parallel to the clamping plane,
the first connecting portion is cranked in a first transition region adjacent to the first coil spring end thereby forming a first crank and the second connecting portion is cranked in a second transition region adjacent to the second coil spring end thereby forming a second crank in order to orient the coil spring longitudinal axis in parallel to the clamping surface,
the first and second cranks are formed as double anglings of the respective first and second transition regions at the respective coil spring ends,
the first connecting portion is angled by a first bend angle in a third transition region adjacent to the first clamping arm, and the second connecting portion is angled by a second bend angle in a fourth transition region adjacent to the second clamping arm.

2. Surgical clip in accordance with claim 1, wherein at least one of:
a) the first clamping arm has a first free end which points in a direction away from the biasing element or substantially away from the biasing element, and
b) the second clamping arm has a second free end which points in a direction away from the biasing element or substantially away from the biasing element.

3. Surgical clip in accordance with claim 1, wherein the clip comprises an intersection region, and wherein the first connecting portion and the second connecting portion intersect in the intersection region.

4. Surgical clip in accordance with claim 1, wherein the first connecting portion and/or the second connecting portion have a flattened portion facing toward the other connecting portion.

5. Surgical clip in accordance with claim 4, wherein at least one of:
a) the flattened portion of the first and/or second connecting portion defines a flattened portion plane, and wherein the flattened portion plane runs perpendicular to the clamping plane,
b) the flattened portion of the first connecting portion directly adjoins the first clamping arm and/or wherein the flattened portion of the second connecting portion directly adjoins the second clamping arm, and
c) the flattened portions of the first connecting portion and the second connecting portion abut against each other or are spaced apart from each other by a narrow gap.

6. Surgical clip in accordance with claim 1, wherein the first connecting portion is angled by a third bend angle between the first clamping arm and the first coil spring end, and/or wherein the second connecting portion is angled by a fourth bend angle between the second clamping arm and the second coil spring end.

7. Surgical clip in accordance with claim 6, wherein the third bend angle corresponds to or substantially corresponds to the fourth bend angle.

8. Surgical clip in accordance with claim 6, wherein the third and/or the fourth bend angle define an interior angle in a range of about 90° to about 120°.

9. Surgical clip in accordance with claim 1, wherein the first bend angle corresponds to or substantially corresponds to the second bend angle.

10. Surgical clip in accordance with claim 1, wherein at least one of:
a) the first and/or the second bend angle define an interior angle in a range of about 90° to about 120°, and
b) the first connecting portion is angled by a third bend angle between the first clamping arm and the first coil spring end, and/or wherein the second connecting portion is angled by a fourth bend angle between the second clamping arm and the second coil spring end, and the first bend angle corresponds to or substantially corresponds to the third and/or fourth bend angle.

11. Surgical clip in accordance with claim 1, wherein the at least one winding comprises at least one first winding portion and at least one second winding portion, and wherein the at least one first winding portion defines a first winding portion plane, and/or wherein the at least one second winding portion defines a second winding portion plane, and wherein the at least one first winding portion and the at least one second winding portion are connected to each other by way of a cranked portion remote from the first coil spring end and from the second coil spring end.

12. Surgical clip in accordance with claim 11, wherein at least one of:
   a) the cranked portion is of rectilinear or substantially rectilinear configuration and is connected to the at least one first winding portion at an angle at a first cranked portion end and is connected to the at least one second winding portion at an angle at a second cranked portion end, and
   b) the cranked portion extends transversely to the first and/or second winding portion plane.

13. Surgical clip in accordance with claim 11, wherein at least one of:
   a) the first winding portion plane and/or the second winding portion plane extend perpendicularly to the coil spring longitudinal axis, and
   b) the at least one first winding portion extends over a first winding portion circumferential angle of less than 360° and/or wherein the at least one second winding portion extends over a second winding portion circumferential angle of less than 360°,
   c) the at least one first winding portion and the at least one second winding portion are separated from each other by a winding portion gap, and
   d) the cranked portion extends transversely at a cranked portion angle of about 45° to the first and/or second winding portion plane.

14. Surgical clip in accordance with claim 1, wherein the coil spring defines a coil spring diameter, wherein the first clamping arm and the second clamping arm have a clamping arm length, and wherein the coil spring diameter is less than the clamping arm length.

15. Surgical clip in accordance with claim 1, wherein:
   the first clamping surface and/or the second clamping surface have a clamping surface structure, and
   the clamping surface structure comprises clamping projections and/or clamping recesses.

16. Surgical clip in accordance with claim 1, wherein the clip at least one of:
   a) is formed as one piece, and
   b) is made from a spring steel wire by means of forming.

17. Surgical clip in accordance with claim 1, wherein a cross sectional area of the clip in a region of the coil spring is smaller than in a region of the first and/or second connecting portion and/or in a region of the first and/or the second clamping arm.

18. Surgical clip in accordance with claim 1, wherein the biasing element holds the first clamping surface and the second clamping surface against each other in the basic position under bias.

19. Surgical clip in accordance with claim 15, wherein the clamping projections and/or the clamping recesses are linear and/or point-shaped.

* * * * *